US009489868B2

(12) United States Patent
Smith et al.

(10) Patent No.: US 9,489,868 B2
(45) Date of Patent: Nov. 8, 2016

(54) DEVICE FOR SIMULATING THE OPERATION OF A MEDICATION DELIVERY DEVICE

(75) Inventors: Christopher James Smith, Frankfurt am Main (DE); Alastair Clarke, Frankfurt am Main (DE); David Sanders, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 924 days.

(21) Appl. No.: 13/123,479

(22) PCT Filed: Oct. 16, 2009

(86) PCT No.: PCT/EP2009/063596
§ 371 (c)(1),
(2), (4) Date: Oct. 1, 2011

(87) PCT Pub. No.: WO2010/046319
PCT Pub. Date: Apr. 29, 2010

(65) Prior Publication Data
US 2012/0015335 A1      Jan. 19, 2012

Related U.S. Application Data

(60) Provisional application No. 61/108,058, filed on Oct. 24, 2008.

(30) Foreign Application Priority Data

Oct. 24, 2008  (EP) ...................................... 08018644

(51) Int. Cl.
*G09B 23/28* (2006.01)
*A61M 5/24* (2006.01)

(52) U.S. Cl.
CPC .............. *G09B 23/28* (2013.01); *G09B 23/285* (2013.01); *A61M 5/24* (2013.01)

(58) Field of Classification Search
CPC ............................. G09B 23/28; G09B 23/285
USPC ......................................................... 434/262
See application file for complete search history.

(56) References Cited

U.S. PATENT DOCUMENTS

| 4,640,686 | A | * | 2/1987 | Dalling et al. | ................. 434/262 |
| 5,567,160 | A | * | 10/1996 | Massino | ........................ 434/262 |
| 5,577,918 | A | * | 11/1996 | Crowell | ......................... 434/319 |
| 7,682,155 | B2 | * | 3/2010 | Raven et al. | .................. 434/262 |

(Continued)

FOREIGN PATENT DOCUMENTS

WO       2008005315 A2      1/2008

OTHER PUBLICATIONS

International Search Report for corresponding International Application No. PCT/EP2009/063596 (3 pages).

(Continued)

*Primary Examiner* — Sam Yao
*Assistant Examiner* — Peter J Alley
(74) *Attorney, Agent, or Firm* — McDonnell Boehnen Hulbert & Berghoff LLP

(57) ABSTRACT

A simulation device for simulating the operation of a medication delivery device comprises a housing (1) and a moveable element (4) partly disposed in the housing (1). The moveable element is moveable from a first position to a second position.

25 Claims, 14 Drawing Sheets

(56) References Cited

U.S. PATENT DOCUMENTS

2003/0230012 A1* 12/2003 Mouyal ..................... 40/124.08
2005/0165363 A1    7/2005 Judson et al.
2007/0292199 A1* 12/2007 Waldinger et al. ........... 401/192
2008/0053460 A1    3/2008 Wilson
2008/0059133 A1    3/2008 Edwards et al.
2008/0249477 A1* 10/2008 Paproski et al. .............. 604/198
2010/0160894 A1*  6/2010 Julian et al. .................. 604/506
2011/0033832 A1*  2/2011 Baba et al. .................... 434/262

OTHER PUBLICATIONS

Communication Pursuant to Rule 114(2) EPC issued in European Patent Application No. 09740878.5 dated Feb. 26, 2016.

* cited by examiner

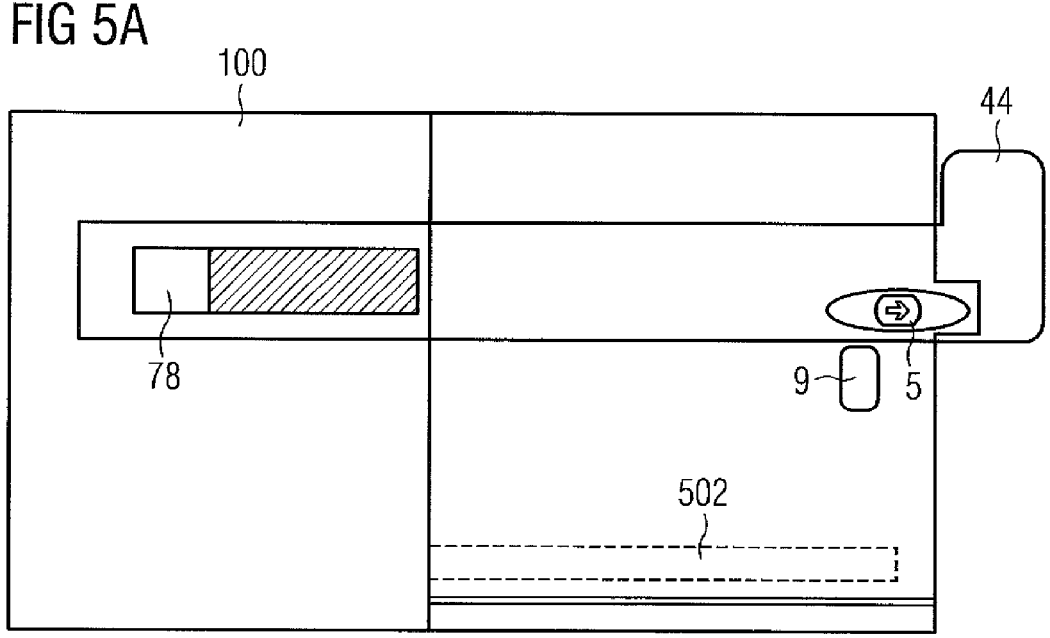

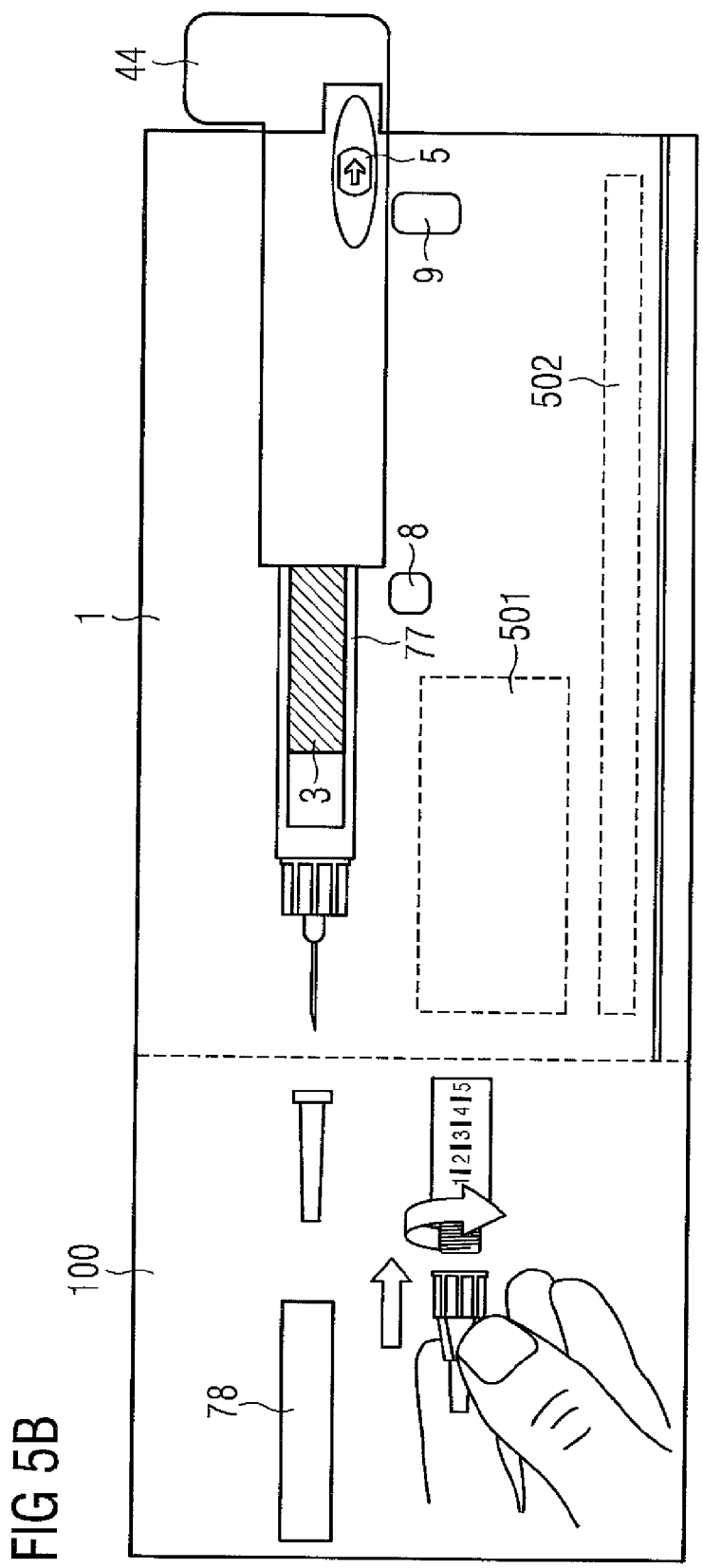

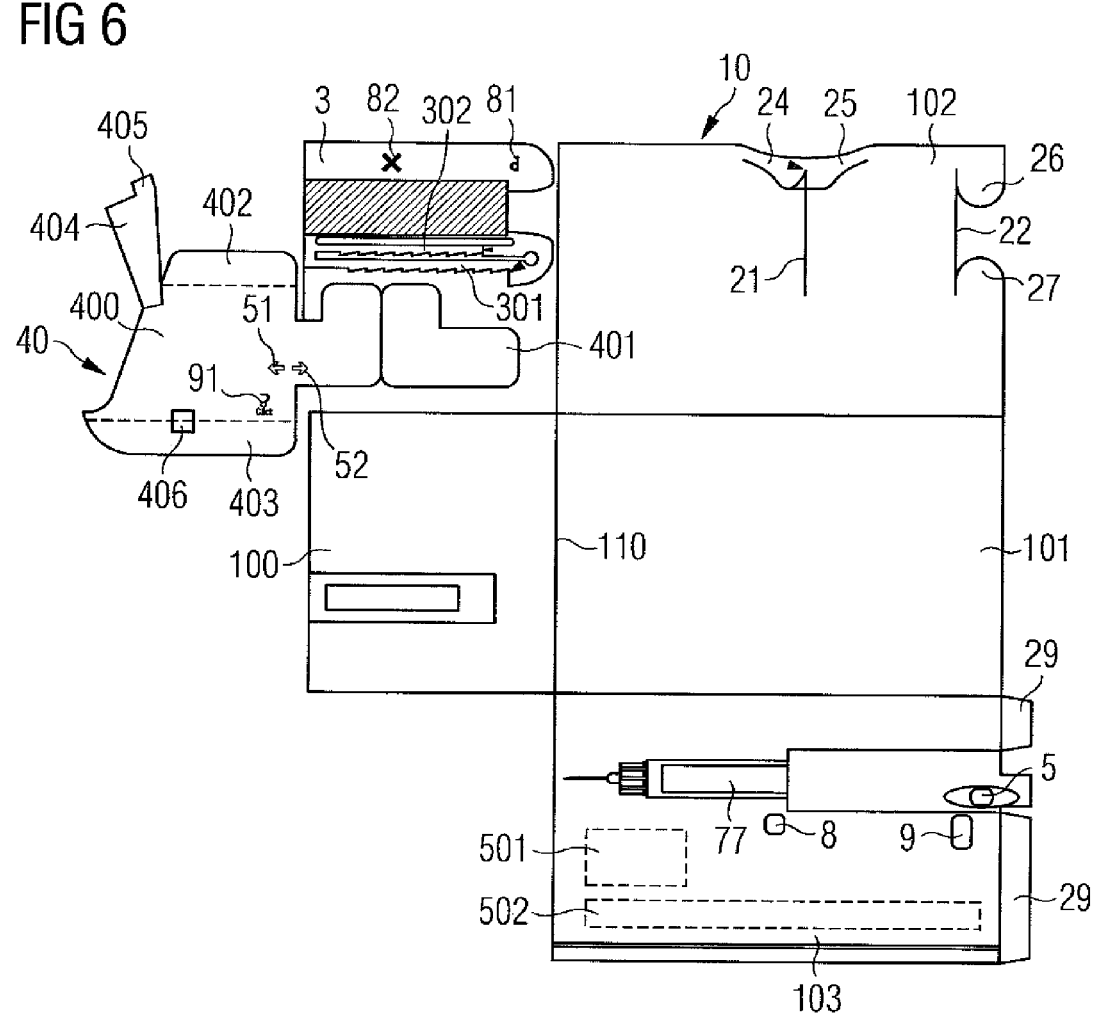

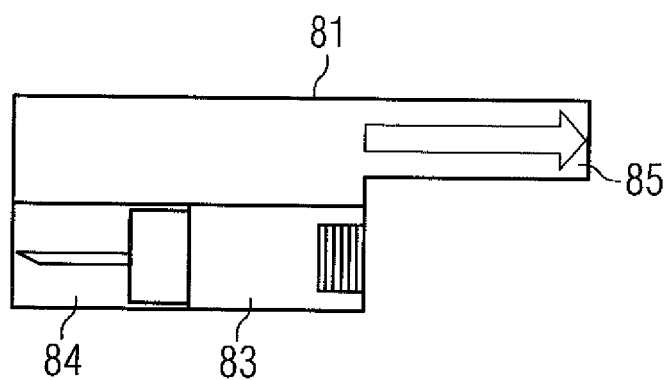
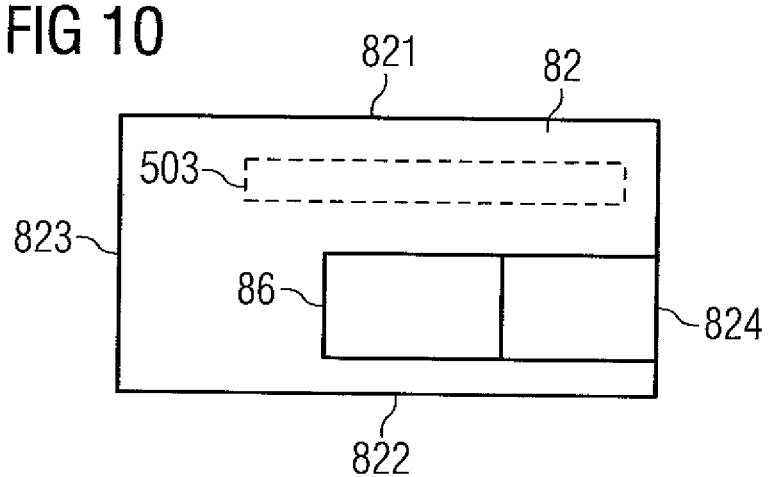

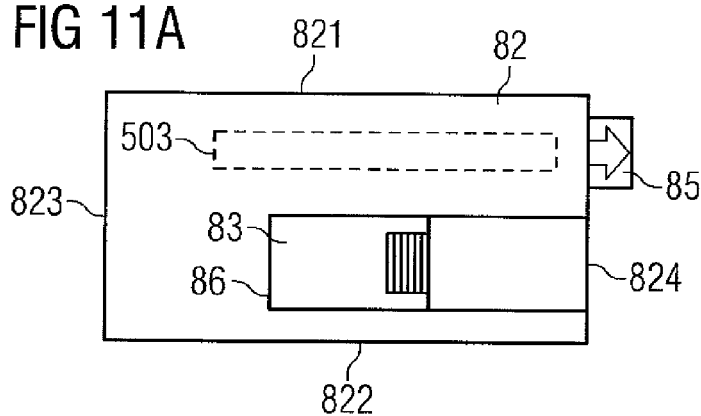
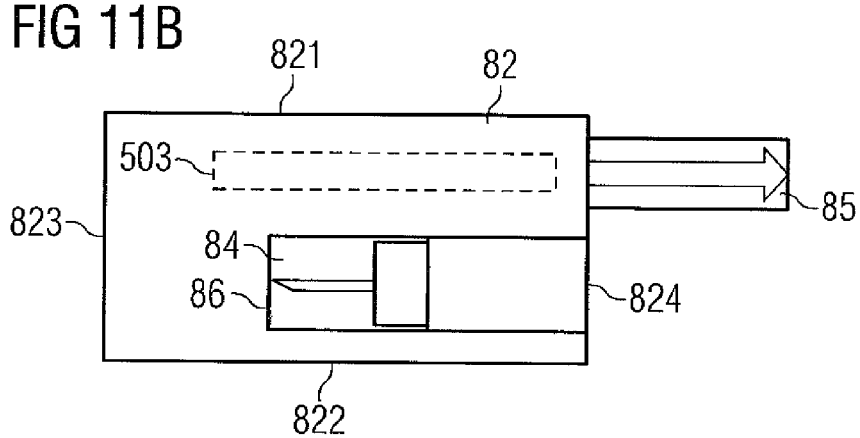
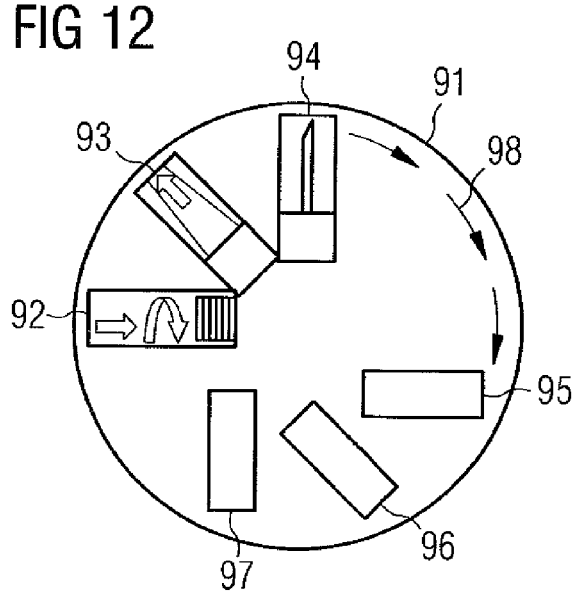

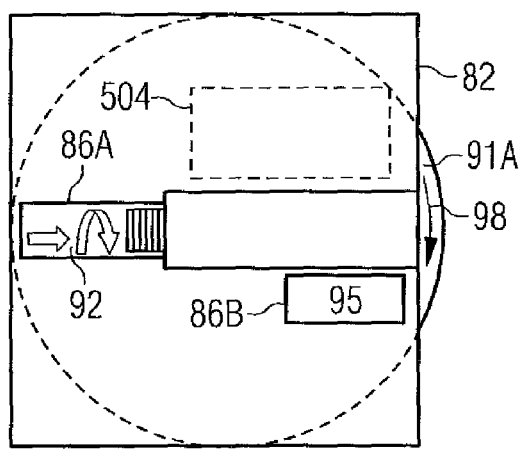
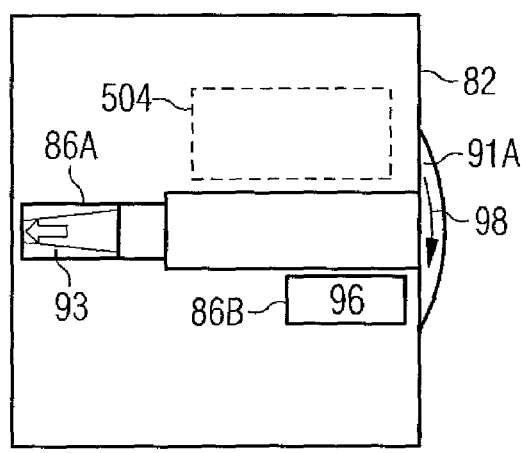
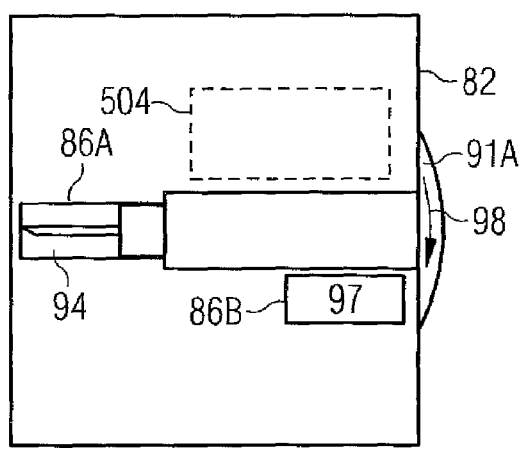

DEVICE FOR SIMULATING THE OPERATION OF A MEDICATION DELIVERY DEVICE

CROSS REFERENCE TO RELATED APPLICATIONS

The present application is a U.S. National Phase Application pursuant to 35 U.S.C. §371 of International Application No. PCT/EP2009/063596 filed Oct. 16, 2009, which claims priority to Provisional Patent Application No. 61/108,058 filed Oct. 24, 2008, which claims priority to European Patent Application No. 08018644.8 filed Oct. 24, 2008. The entire disclosure contents of these applications are herewith incorporated by reference into the present application.

The present invention relates to a simulation device for simulating the operation of a medication delivery device.

Medication delivery devices, e.g. injection pens, auto-injectors or inhalers, have been developed to facilitate the self-administration of medication.

Simulation or training devices in the field of simulating medication delivery devices, e.g. injection pens, are commonly used when patients are trained.

Document U.S. Pat. No. 5,567,160 discloses a training device for training individuals to use automatic injectors. The training device comprises a spring which is manually compressed and then released when an activating button is moved. This document concerns an autoinjector device simulator, which is a single-use device to deliver a single dose of medication, e.g. for emergency use. The simulator is in the same form as the autoinjector device, which means the simulator replicates the three-dimensional appearance of the autoinjector device and contains numerous components.

Document US 2008/0059133 discloses an electronic simulated medical delivery device coupled to an electronic circuit system.

There are a number of problems that may arise with typical training devices. They may be often designed to very closely resemble the actual medication delivery device that they are simulating. Indeed training aids may be often produced where the actual device components are used with the exception of a colour or labeling change and where the medication container is replaced with a container of a suitable placebo, e.g. water-for-injection or saline solution.

This creates the possibility that the patient may confuse the training aid with the actual device and deliver a dose of placebo rather than medication or vice versa. Such training aids may also be more costly than the actual device mechanism because the training aid is typically manufactured in smaller volumes. A further disadvantage for using actual device components is that it requires manufacturing capacity that could otherwise be utilised to manufacture the actual device.

Training aids that merely simulate an actual medication delivery device also suffer the disadvantage that they serve only to facilitate practise with the device, rather than providing any training information or instruction. The user may therefore require training in the operation of the training aid.

It is an aim of the present invention to provide a simple and inexpensive simulation device. A further aim of the present invention is to provide a simulation device that provides additional information and instruction to the user. For this purpose, a simulation device for simulating the operation of a medication delivery device is provided. The simulation device comprises a housing and a moveable element partly disposed in the housing. The moveable element is moveable from a first position to a second position for simulating at least one feature of an actual medication delivery device. "Moveable" means that the moveable element is moveable in an axial direction and/or rotatable and/or pivotable and/or is able to pop up.

The moveable element may e.g. simulate a needle unit, a cap, a trigger, a slider, a medication cartridge or cartridge holding component or device cover or a button. Preferably the moveable element is a button element which simulates a button.

This simulation device may or may not simulate all of the features of an actual device. It is preferable to only simulate the features of the actual device that are crucial to the patient's understanding of the operation of the actual device. In one embodiment, the simulation device enables to mimic the use of a multi-dose pen-type injector, where for example several doses can be delivered from a cartridge of medicament. In one embodiment, the simulation device enables to mimic the use of a fixed-dose pen-type injector. Such simulation device may be able to simulate the attachment of a disposable needle.

An actual device, selected features of which can be simulated by the inventive simulation device, comprises a cartridge filled with a medication, e.g. a liquid drug.

When doses are ejected with an actual medication delivery device the cartridge bung advances along the cartridge in the distal direction expelling the medicine through a delivery means, e.g. a needle. The fluid pressure of the liquid drug in the cartridge and friction between the bung and the cartridge internal surfaces counteracts the movement of the bung.

The inventive simulation device is a pure simulation device simulating features and the operation steps of an actual medication delivery device without using actual medication. The simulation device is neither capable of providing nor capable of administering a medication, e.g. a liquid drug, or a medication simulating substitute, e.g. water or placebo.

This simulation device eliminates the risk of the patient attempting to administer from it or mistaking the simulation device for the actual medication delivery device. Further, this simulation device would minimize the production costs compared to using some or all of the components of the actual device. Additionally the materials selection, size, shape and markings of the simulation device make it obvious to the user that this is not the actual medication delivery device.

One embodiment of the simulation device comprises a wheel at least partly disposed in the housing. The moveable element is coupled to the wheel such that the wheel rotates in response to moving the moveable element from the first position to the second position.

In one embodiment, the simulation device comprises a display element configured to display status information and/or instruction information which changes when the sliding element moves.

In one embodiment, the simulation device comprises a sliding element at least partly disposed in the housing. The moveable element, preferably a button element is coupled to the sliding element such that the sliding element is moved in a direction to the distal end in response to moving the moveable element from a first position to a second position. The sliding element simulates the movement of a piston and/or bung advancing along the medication container.

In one embodiment, the sliding element is constructed to move from a starting position to a final position, which visually simulates the movement of a piston or bung element or a piston rod driving a piston or bung element inside a cartridge of an actual medication delivery device.

A reusable embodiment of the simulation device comprises a sliding element resettable to the starting position. An expendable embodiment of the simulation device comprises a sliding element which is not resettable to the starting position.

In a preferred embodiment, the simulation device comprises a ratchet device releasably coupled to the sliding element such that the sliding element moves in the distal direction in response to moving a button element from the first position to the second position. The first position is the furthest proximal position of the button element. The second position is the furthest distal position of the button element fully pushed into the housing. Preferably, the ratchet device is releasably coupled to the sliding element such that the sliding element does not move in a proximal direction in response to moving the button element from the second position to the first position.

In one embodiment the simulation device comprises a spring element and/or damper element releasably coupled to a button element and/or to a sliding element such that the button element is moved from the first position to the second position in response to pushing the button element with at least a given force. The inclusion of a plastic or metal spring can provide tactile feedback to the user in order to simulate the forces required to operate the actual device. For example if the actual device is an injection device force will be required to drive a rubber bung along the length of the cartridge and/or to eject medication from a needle. Furthermore the spring element can provide audible feedback to the user. Thus, the spring element is appropriate to simulate an internal feature of the actual medication delivery device. In one embodiment the spring element is designed to reset the button element into the first position after pushing the button element to the second position.

In a further embodiment, the display element of the simulation device is suitable for displaying the position of a sliding element. The sliding element simulates the travel of the bung in the cartridge of an actual device. This display element simulates the transparent nature of the cartridge.

In one embodiment, the simulation device comprises a second display element constructed to simulate a display element present in the actual device. The second display element displays status information which corresponds to the position of a sliding element and/or button element. This display element may display a first direction mark (symbol or colour, e.g. an arrow in the distal direction) when the button element is positioned in the first position and/or a second direction mark (symbol or colour, e.g. an arrow in the proximal direction) when the button element is positioned in the second position. These marks replicate symbols present in the actual device and may be used to indicate to the user whether to pull the button element to simulate setting a dose or to push the button element to simulate delivering a dose. Alternatively this second display element may display a number corresponding to the volume of the medicament dose that would be delivered by the actual device if the same user actions were followed.

In one embodiment, the simulation device comprises additional display elements constructed to display further instructional information or feedback to the user, for example corresponding to the position of the sliding element and/or button element, that is not present on the actual device. For example a display element may indicate to the user that a simulated priming dose should be completed or inform the user of the completion of the simulated injections. In this example the display element would display a starting status mark when the sliding element is positioned in the starting position and/or a final status mark when the sliding element is positioned in the final position. Display elements may also provide status information in numeric or text form. For example, a display element may be used to numerically indicate the number of simulated doses remaining or the amount of simulated medicament remaining in the simulation device.

Preferably, at least one of the display elements comprises a window (e.g. in the housing) such that the displayed information is visible through the window. This window may be an uncovered opening or may be covered by a transparent material. In one embodiment a dose scale is provided to resemble a graduated scale of a medicament container.

In one embodiment, the simulation device comprises a hub element suitable for releasably attaching a needle unit. It should be mentioned that a needle unit means an actual needle, identical to those used for the actual device, or a needle dummy. Preferably, the needle unit means a needle dummy which helps to prevent injuries during training sessions. Attaching and detaching needles is a particularly difficult operation for injection pen users as fine manual dexterity is required to orientate and align the needle with the needle hub. If this is practised with an actual pen, it may cause the cartridge septum to become pierced and possibly damaged. Therefore, it is advantageous if the simulation device could be used to practise needle attachment and detachment.

In one embodiment, at least one of the elements of the simulation device is made of plastic. In one embodiment, at least one of the elements of the simulation device is made of laminated composite foam-board. In one embodiment, at least one of the elements of the simulation device is made of paper or cardboard.

Preferably most or all elements of the simulation device are made of inexpensive material, most preferably of cardboard. Another material which can be used for the simulation device is injection moulded plastics. Thus, it would be possible to include a simulation device to serve as training aid in each package of the actual medication delivery device or to supply simulation devices to healthcare professionals, e.g. doctors, nurses or pharmacists, or directly to patients in order to aid patient training.

The cost of the simulation device may be reduced by using low cost materials, for example card, composite foam or card, low cost plastic mouldings or pressings. In a preferred embodiment, the housing of the simulation device is formed as a card having at least two layers. In one embodiment, at least one of the elements of the simulation device is folded. The card would be printed in a way that all or a portion of the card resembles the actual medication delivery device for which the training aid is intended. The card may or may not include additional instructions, warnings or explanatory messages.

Additionally or alternatively, cost may be reduced by only simulating aspects of the medical device that are essential for teaching the correct use of the actual device and intentionally omitting other features of the device which may complicate the simulation device and which do not add significantly of the patient's learning. The resulting simulation device will resemble the actual device, but not necessarily in 3D (the three-dimensional appearance) or in the use of materials. The simulator may be merged into a "working instruction booklet", which may comprise three-dimensional or moveable parts, for example pop-up parts. This gives the opportunity for including additional instructions or moving features or display windows that are not part of the actual device, for example being parts of an attached instruction card or booklet.

In one embodiment the simulation device cannot be reset to its starting state once the sliding element has reached its end position. This disposable simulation device is suitable for demonstrating that the actual medication delivery device is not reusable. In a preferred embodiment the simulation device will replicate the end of life condition of the actual device. For example once all of the simulated doses have been delivered it will not be possible for the button element to be moved from the second position to the first position.

However, reusable simulation devices, such as might be required for repeated demonstrations in doctors' offices or hospitals, might be better embodied with more robust material, such as plastic. Some features, such as audible clickers or plastic springs, may only be possible using plastic components rather than card.

In a further embodiment a simulation device is provided suitable to simulate multiple devices within one housing. For example, the housing may contain a number of button elements and sliding elements.

Other features will become apparent from the following detailed description when considered in conjunction with the accompanying drawings.

FIG. 5A shows a further embodiment of a simulation device made of cardboard in a "closed" position.

FIG. 5B shows the simulation device embodiment of FIG. 5A in an "open" position

FIG. 6 shows a two dimensional flat blank having solid contour lines indicating either folds or divisions between components which can be used to manufacture the embodiment of a cardboard simulation device shown in FIG. 5.

FIG. 9 shows an embodiment of a slider.

FIG. 10 shows an embodiment of a housing.

FIGS. 11A and 11B show an embodiment of a simulation device for simulation of attaching a needle unit, the simulation device comprising the slider and the housing.

FIG. 12 shows an embodiment of a rotating wheel for a simulation device.

FIGS. 13A, 13B and 13C show the simulation device comprising the wheel.

Figure 14A:
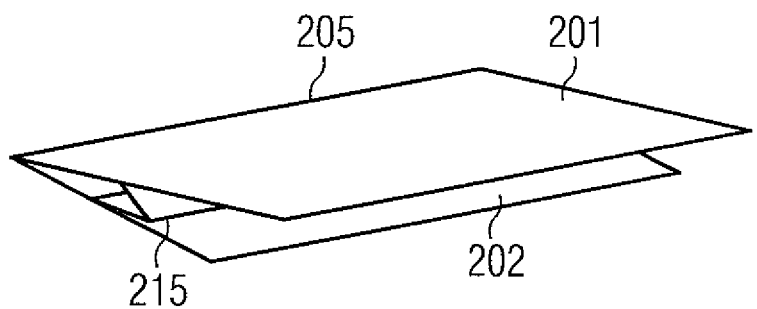
Figure 14B:
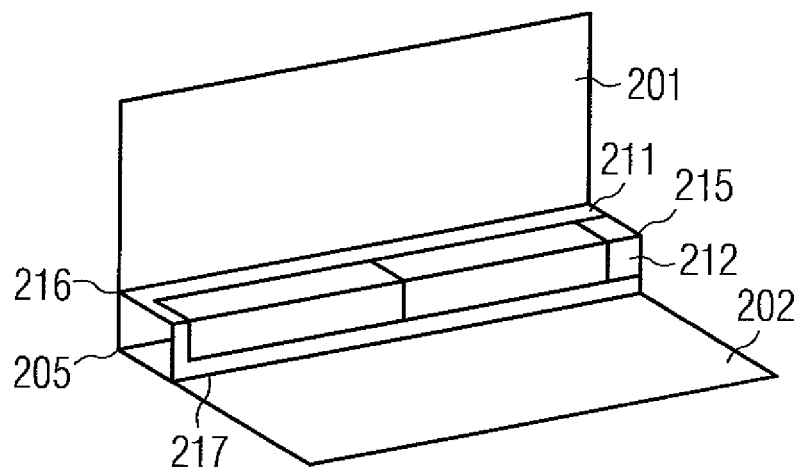

FIGS. 14A and 14B show a simulation device designed as a pop-up card. FIG. 14A shows the folded pop-up card. FIG. 14B shows the open pop-up card.

Figure 15A:
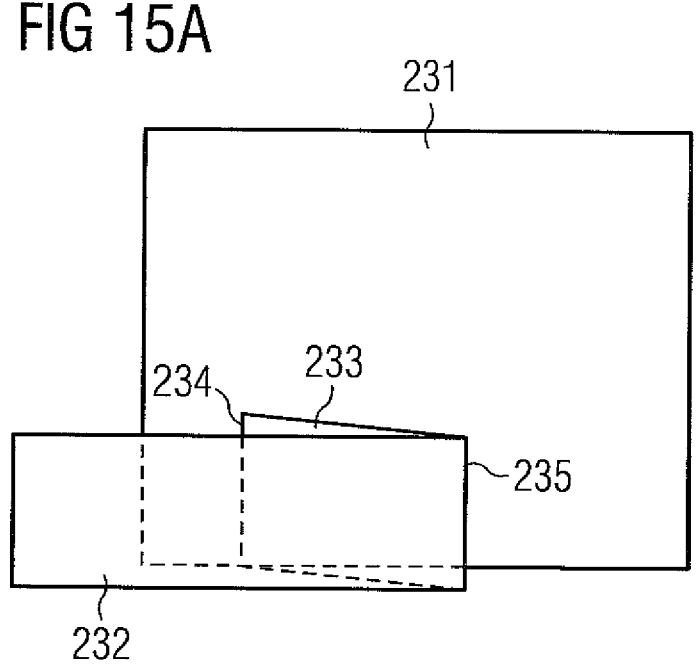
Figure 15B:
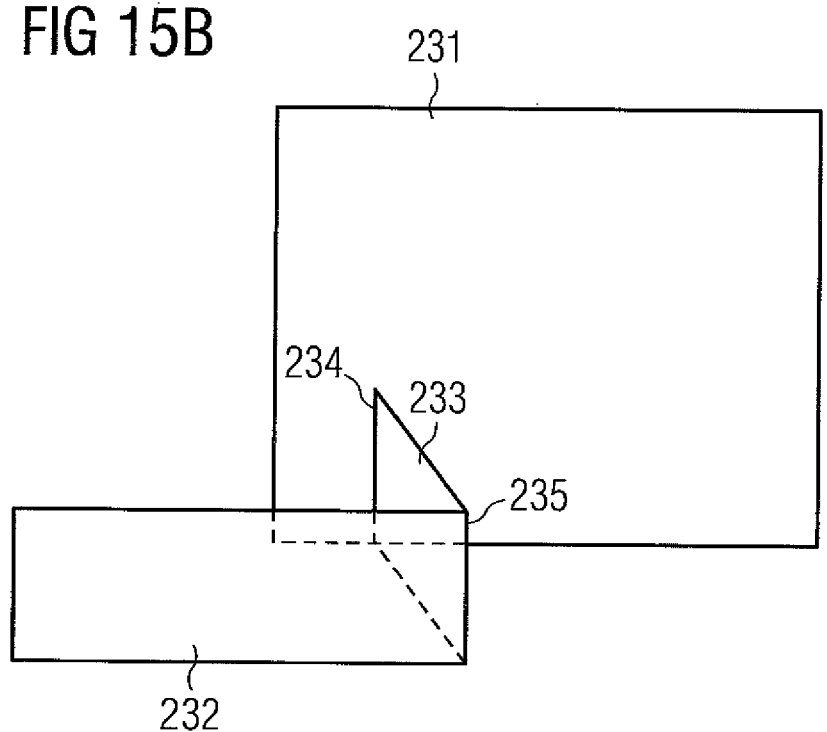

FIGS. 15A and 15B show an embodiment having a hinged section.

Figure 16A:
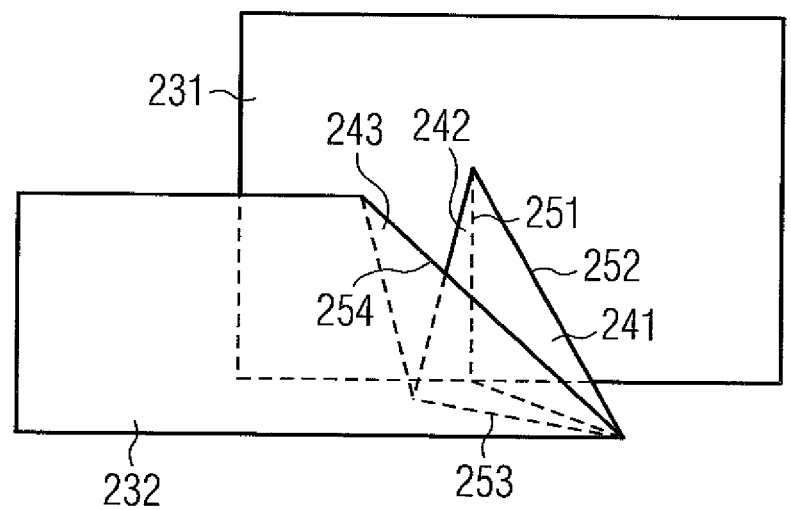
Figure 16B:
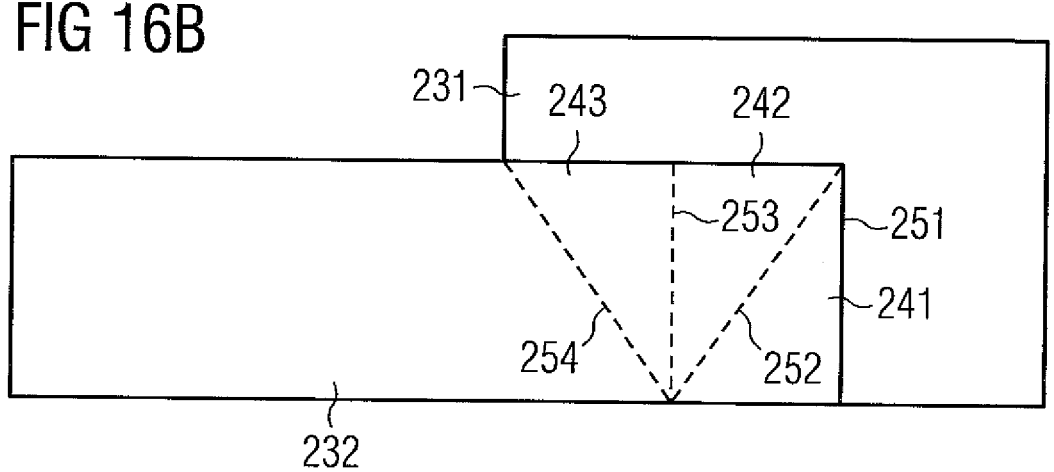

FIGS. 16A and 16B show an embodiment with angled folds.

Figure 17:
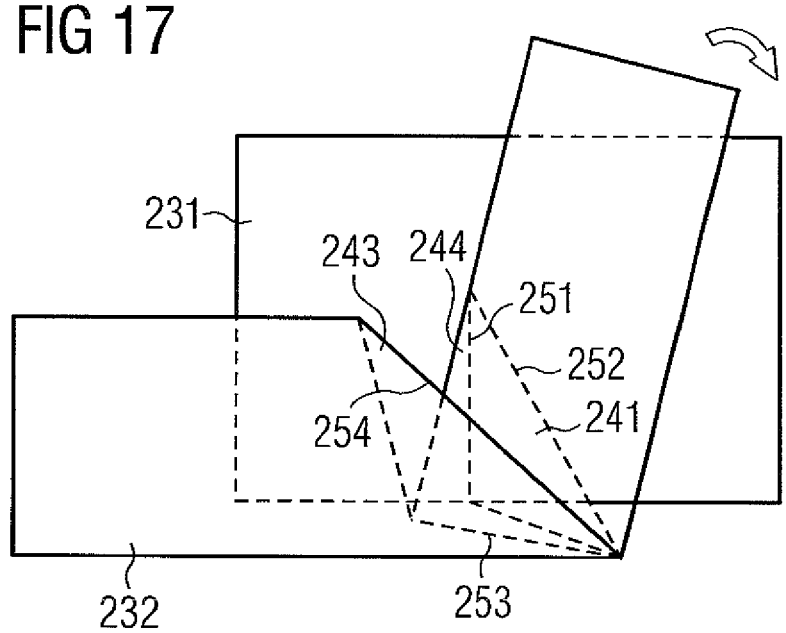

FIG. 17 shows a further embodiment with angled folds.

FIGS. 18A, 18B, 18C and 18D show an embodiment of a simulation device which simulates a dry powder disk inhaler.

Figure 1:
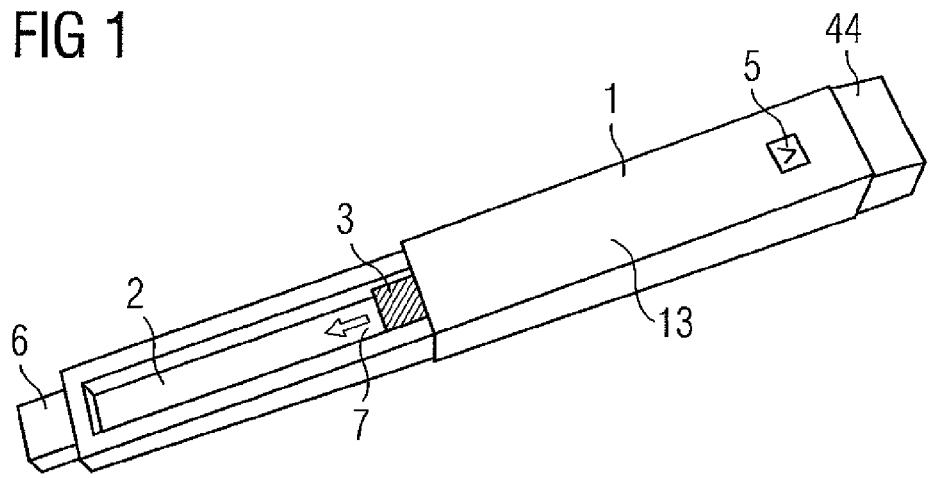
FIG. 1 is a perspective view of an embodiment of a simulation device for simulating functions of a medication delivery device.

In FIG. 1, a perspective view of an embodiment of a simulation device for simulating functions of a medication delivery device or medicament delivery device, e.g. an injection pen, is shown.

The simulation device comprises a housing 1 having a distal end and a proximal end. A slot 2 extends from a front part of the housing 1, which is the distal end, to a rear part of the housing 1, which is the proximal end. A first part of the slot 2 located near the rear part of the housing 1 is covered by a housing cover 13 which is part of the housing 1. The slot 2 located near the front part of the housing 1 is visible from the outside.

A push-pull button element 4 (see FIG. 3) comprising a button grip 44 is partly located in the slot 2 in the rear part of the housing 1 such that only the button grip 44 is visible. The button element is constructed to be pulled into a first position and to be pushed into a second position. FIG. 1 shows the pushed button element being in the second (distal) position.

A sliding element 3 is disposed in the slot 2 of the housing 1. In FIG. 1, the sliding element 3 is disposed in a starting position such that only a small part of the sliding element 3 is visible in the visible part of the slot 2 located in the front part of the housing 1. After pulling the button element 3 from the second position to the first position, the sliding element 3 is then moved in a distal direction in response to moving the button element in the distal direction from the first position to the second position. In other words, by pushing the button grip 44 into the housing 1, the sliding element 3 travels in the direction indicated by the arrow.

The sliding element 3 merely slides distally inside the slot 2. When the button element 4 is moved from the first position to the second position, dry friction counteracts the distal movement of the sliding element.

The not covered part of the slot 2 in the front part of the housing 1 is visible from the outside and serves as a status display 7. The position of the sliding element 3 indicates how far the simulated bung has advanced along the cartridge. The position of the sliding element 3 in conjunction with the dose scale printed on transparent window 14 (not shown) indicates how many simulated doses remain in the simulation device. The movement of the sliding element 3 simulates the movement of the bung in the cartridge of an actual medication delivery device. The position of the bung in the cartridge indicates the residual amount of the medication in the cartridge.

A window 5 in the housing cover 13 serves as direction indication display indicating in which direction the button element is to be moved. The display in the direction indication window 5 changes depending on the position of the button element. FIG. 1 shows an arrow in the direction indication window 5. The arrow indicates that the button element should be pulled proximally. After pulling the button element another arrow would be visible in the direction indication window 5 indicating that the button element should be pushed distally.

A hub element 6 is arranged at the front of the housing 1. The hub element 6 may comprise connection means so that a patient could practise attaching a needle or a needle dummy on the hub element and detaching the needle or the needle dummy for the purpose of simulating attaching and detaching a needle on/from a connection means. Preferably the hub element will use similar needle connection means as the actual medication delivery device, e.g. a screw thread, a bayonet lock or a snap lock.

Even if the simulation device does not feature the full 3D shape of the needle connection means, different embodiments of hub elements are suitable for simulating attaching and detaching a needle unit. A cardboard simulation device could be manufactured with serrations on the hub element to mimic a sufficient portion of a screw thread to provide the connection means for attaching needles. Similarly, a plastic embodiment or a plastic needle hub added to a substantially cardboard embodiment of the simulation device could feature similar serrations or indeed a full or partial section of the connection means, e.g. a screw thread. In both cases the internal (distal) end of the needle would enter an air space in the simulation device instead of piercing a septum of a cartridge.

The embodiment shown in FIG. 1 is designed to resemble and simulate an actual pen injector which is a fixed-dose injection device. An embodiment of the actual pen injector may deliver a fixed number of doses from a cartridge of medication. Once the dose is set it cannot be cancelled without delivering the medication. The embodiment of the simulation device simulating this injector pen is particularly well-suited to the pen because the pen dose button is operated by pulling and pushing which can be simulated relatively easily.

The simulation device shown in FIG. 1 serves as training aid, based on the fixed-dose injection pen. The button element of the simulation device simulates a moving pull-push dose button of an actual injection device. The setting of the injection pen is simulated by pulling the button grip in the proximal direction. A cartridge bung which advances a fixed distance for each dose along the cartridge when doses are ejected is simulated by the sliding element 3 advancing along the slot 2 when the button grip 44 is pushed.

Another embodiment of the simulation device, which is not shown, has a rotating button grip. This could be obtained with simple injection mouldings or cardboard tubes. A simulation device with a rotating button grip can be used to simulate a number of medication delivery devices, including variable dose injection pen, such as those used for insulin delivery.

One further embodiment is suitable for simulating some of the internal features of the actual medication delivery device. For example, the force required to move a rubber bung along the length of the cartridge or the sounds made by the actual medication delivery device during setting and/or delivering a dose could be simulated by the inclusion of a plastic or metal spring in the simulation device providing a tactile or audible feedback. The spring can be coupled to the button element such that a given pressure is necessary to push the button element. In an alternative embodiment, the spring is coupled to the sliding element. In one embodiment the spring is arranged such that it is compressed in response to pushing the button element, e.g. by positioning the spring between the sliding element and the front housing wall. Alternatively, the spring is arranged such that the spring is uncompressed or expanded in response to pushing the button element.

The simulation tool is used for training patients and demonstration purposes. When a patient is given a medication delivery device he or she needs to be trained in the safe and correct use of this device by a medical professional. In addition or if no training is provided, the patient may benefit from practising the use of the device. Such practice might involve seeing how far the button should move, observing any changes in the device during operation, e.g. feedback/printing in status display windows, reading the dose scale or remaining doses indicators, attaching and detaching the needle. If this practice is performed using the actual medication containing device that patient will waste medication and there is the risk that the patient might damage the device or act in an unwise or unsafe manner.

One embodiment of the simulation device is designed to closely resemble, in terms of colours, printing, external moving parts and overall size, an actual medication delivery device. Each different medication delivery device would have its own version of the simulation device. The simulation device is far simpler, and therefore less costly, than the actual device. The simulation device would not necessarily have the same 3D shape as the actual device and does not contain any medication or liquid.

The embodiment as shown in FIG. 1 is made of three layers of foam-board. Foam-board is a sandwich structured composite comprising a top and a bottom layer and layer of filling material sandwiched in between the top and the bottom layers. The layer of filling material is a foam layer, e.g. foamed plastic, laminated between two sheets of cardboard. An advantage of this material is that the three layers of foam-board give the simulation device a similar thickness to the actual medication delivery device. Therefore the shape of the simulation device may more closely resemble the three-dimensional shape of the actual device compared to using thinner materials. However, a simulation device that is an exact reproduction of the shape of the actual device is most likely unnecessary to train the patient in the correct operation of the actual device. Therefore less costly materials, such as card or cardboard, may be substituted.

Figure 2:
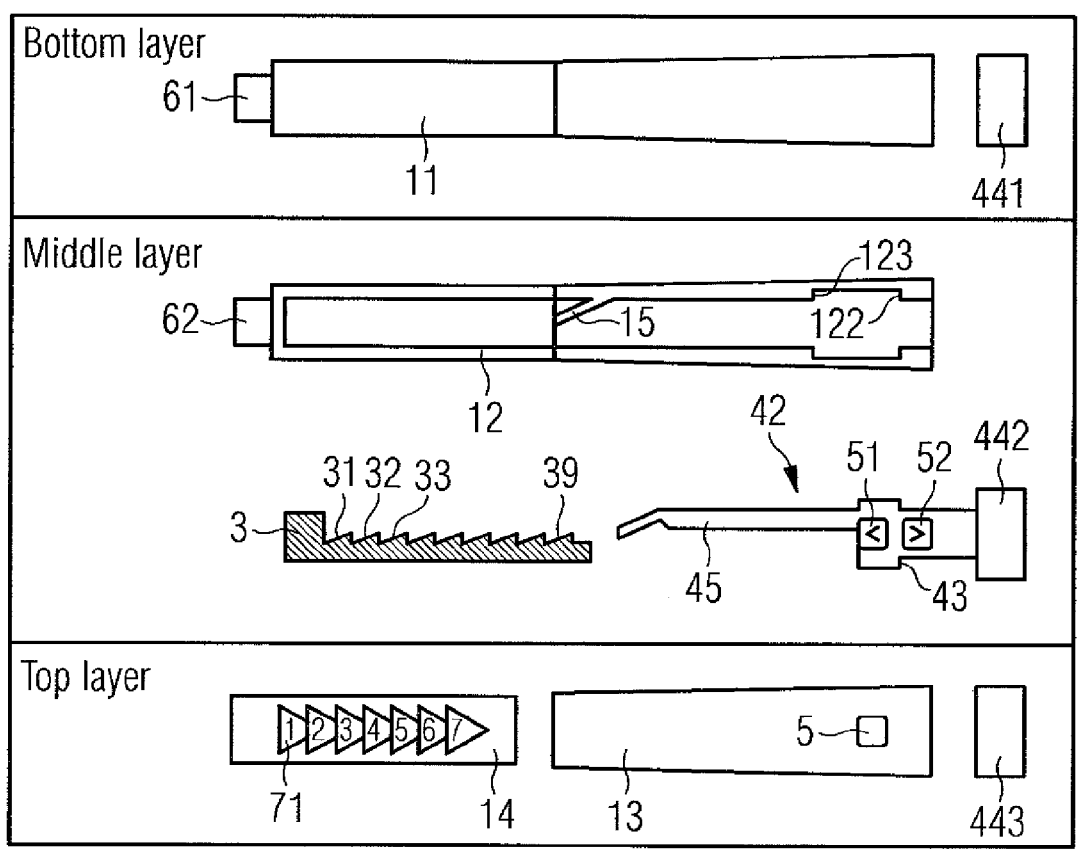
FIG. 2 shows a top view of foam-board components suitable for manufacturing the embodiment as shown in FIG. 1.

FIG. 2 shows a top view of foam-board components suitable for manufacturing the embodiment as shown in FIG. 1.

The embodiment of the simulation device is made of three layers of foam-board components. There are bottom, middle and top layer components.

The bottom layer of the simulation device comprises two components. A bottom part 11 of the housing comprising a bottom part 61 of the hub section serves as a base. A bottom part 441 of the button grip is provided to give the button grip 44 the same thickness as the housing 1.

The middle layer of the simulation device comprises three components. A housing wall section 12 comprising a top part 62 of the hub section, defines the walls of the housing and provides limits for button element and sliding element travel. The housing wall section 12 comprises a flexible arm 15 constructed to act as a pawl of a non-return ratchet. The housing wall section 12 is adhered to the bottom part 11 of the housing. The housing arm 15 is left free of adhesive and is not adhered to the bottom part 11 of the housing.

The sliding element 3 is constructed as a linear rack comprising a set of ratchet teeth 31, 32, 33, 39.

The middle layer part 42 of the button section comprises the middle layer part 442 of the button grip, a locking element 43 and an extended ratchet arm 45. Marks 51, 52 suitable for indicating the position of the button element are printed on the middle layer part 42 of the button element. The marks are visible in the direction indication window 5 of the simulation device.

The width of locking element 43 is larger than the width of the part 41 of the button element which is pulled out when the button grip 44 is pulled. Thus, the locking element 43 stops the proximal travel of the button element when reaching the inside wall 122 of the rear of the housing wall section 12, the inside wall 122 stopping the proximal movement of the locking element 43. The distal movement of the button element is stopped when the button grip 44 reaches the rear edge of the housing and/or when the locking element 43 reaches a stopping corner 123 in the inside wall of the housing wall section 12.

The top layer of the simulation device comprises three components. A first housing cover 13 comprises an opening 5 serving as direction indication window through which the marks 51, 52 on the button element can be seen. One of the marks 51, 52 appears depending upon the position of the button element in the direction indication window 5.

The first housing cover 13 covers the slot 2 located near the rear of the housing 1. In one embodiment, the first housing cover 13 is hinged to the middle and bottom layers to provide access to reset the middle layer components.

A second housing cover 14 comprises a cartridge dose scale 71 made of transparent material, e.g. cellophane, onto which the cartridge label or graduated dose scale could be printed. It should be mentioned that the second housing cover 14 is not shown in the embodiment shown in FIG. 1.

A top layer part 443 of the button grip is adhered to the middle layer 442 of the button grip to give the button grip 44 the same thickness as the housing 1.

The externally visible surfaces may be shaped and printed in a way to resemble the actual medication delivery device for which the simulation device is intended.

Figure 3:
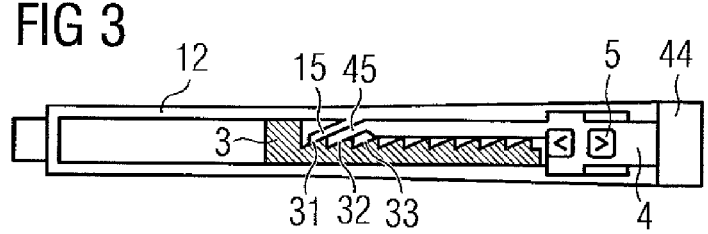
FIG. 3 is a top view of the middle and bottom layers of the embodiment assembled from the components shown in FIG. 2.

FIG. 3 is a top view of the embodiment comprising the bottom and middle layer components shown in FIG. 2. The sliding element 3 and the button element 4 are arranged in a starting position.

The sliding element 3 is positioned such that the housing arm 15 engages the depression in front of the first tooth 31 of the sliding element 3. The button element 4 is in the second (pushed in) position. The ratchet arm 45 of the button element 4 is engaged with the depression in front of the second tooth 32.

When the button element 4 is pulled, the ratchet arm 45 deflects or slides up and over the second tooth 32 and is forced back (e.g. by the elasticity of the arm 45) into the depression in front of the next tooth 33. When the button is pulled in the proximal direction the sliding element 3 is prevented from also moving in the proximal direction by housing arm 15.

When the button element 4 is pushed in the distal direction, the angle of the button element's ratchet arm 45 causes it to bear against the second tooth 32, forcing motion of the sliding element 3 in the distal direction as the button element 4 is moved. The housing arm 15 deflects or slides up and over the first tooth 31 with the elasticity of the arm, which forces it back into the depression in front of the next tooth 32. In one embodiment, the relative movement of the ratchet components is accomplished by a bowing or twisting of the rack or pawl rather than by elastic deformation.

The step-by-step travel of the sliding element 3, by repeated pulling and pushing the button element 4, continues until the ratchet arm 45 has slid over the last tooth 39. Furthermore, the sliding element 3 has reached the front wall of the housing which limits the travel of the sliding element 3.

FIGS. 4A to 4F illustrate various steps in the operation of the simulation device.

The user steps, the movement of the bung simulating sliding element 3 and the contents of the direction indication window 5 of the simulation device are similar to an actual embodiment of a pen injector.

Figure 4A:
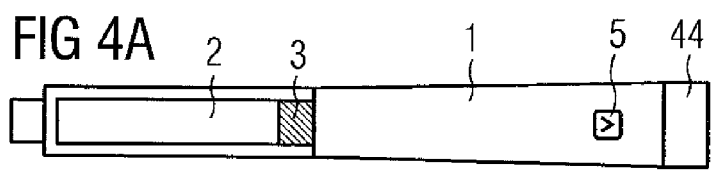
FIGS. 4A to 4F illustrate a number of steps in the operation of the simulation device illustrated in FIGS. 1 to 3.

The initial status of the training aid, as described in relation with FIGS. 1 and 3, is shown in FIG. 4A. The button grip 44 is in a pushed in state. The sliding element 3 is in its most proximal position. In the window 5 an arrow is visible which is pointing in the proximal direction.

Figure 4B:
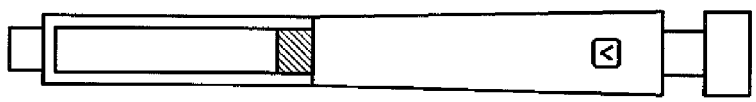

Simulating the setting of a dose of medication, the user pulls out the button grip 44 of the button element 4 to its furthest proximal position, as shown in FIG. 4B. The movement of the button element 4 is stopped when the locking element 43 reaches the end of the slot on the inside wall 122 of the housing middle layer 12. After pulling the button element 4 proximally, an arrow pointing in the distal direction is displayed in the direction indication window 5. This arrow indicates to the user that the next movement of the button element 4 to perform the next step in the operation of the device would be to push the button grip 44 distally. When button element 4 is pulled proximally, the end of the ratchet arm 45 flexes over one tooth of the sliding element 3 and springs back ready to engage this tooth on the button element's inward stroke. The material of the ratchet arm 45 does not actually need to be flexible to achieve this. Flexibility can be achieved in a card embodiment by suitable scoring or folding. The sliding element 3 is prevented from travelling outwards with the button element 4 by a combination of friction between the sliding element 3 and the housing walls and by being engaged by the housing arm 15 of the housing wall section 12.

Figure 4C:
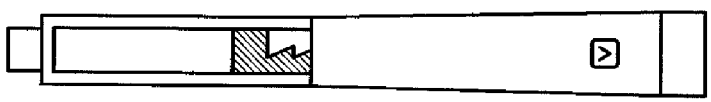
Figure 4D:
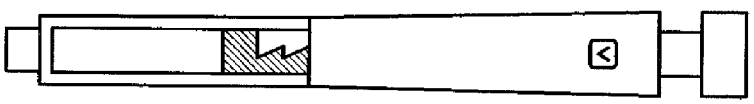

Simulating administering the dose, the user pushes the button grip 44 distally fully back in, as shown in FIG. 4C. The distal travel of the button element 4 is limited by reaching the stopping corner 123 on the inside wall of the housing wall section 12. An arrow pointing in the proximal direction is displayed in the status window. The end of the ratchet arm 45 drives against the engaged tooth of the sliding element 3. The sliding element 3 is advanced by one step simulating the injection of one dose. As the sliding element moves, the housing arm 15 flexes to allow the next ratchet tooth to pass. The flexibility can be achieved in a card embodiment by suitable design and possible scoring or folding of the arm.

Figure 4E:
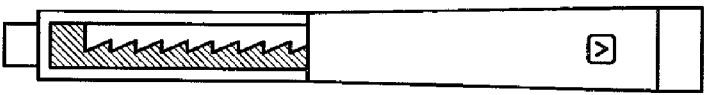

Simulation of dose setting and administration can be repeated until the sliding element 3 is fully advanced, the sliding element 3 simulating that the plunger of an actual device reaches the end of the cartridge of the actual device, as shown in FIG. 4E.

Figure 4F:
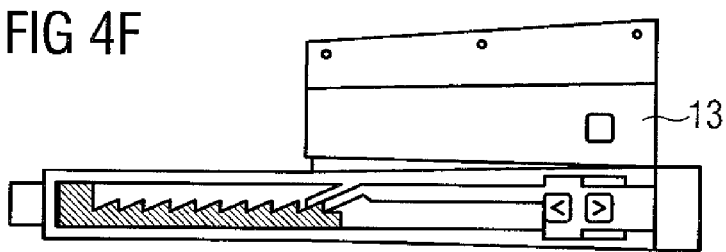

In one embodiment the simulation device cannot be reset to its starting state once the sliding element 3 has reached its end position as shown in FIG. 4E, thereby simulating a disposable medication delivery device which is also locked in its end position and not resettable. FIG. 4F shows another embodiment wherein the sliding element 3 is positioned in the final position. In this embodiment, the first housing cover 13 is hinged to the middle and bottom layers to provide access to reset the middle layer components. The housing cover 13 on the top layer is opened in order to access the sliding element 3 and return it to its starting position, thereby simulating a resettable medication delivery device or allowing the multiple use of the simulation device for training purposes.

There are a number of options for multiple use of the simulation device. One embodiment of the simulation device is sufficiently simple that there are no parts to prevent reuse. Alternatively, if each use of the simulation device has an effect on the simulation device, for example advancing the sliding element simulating the piston, then there can be a reset mechanism for resetting the sliding element which reverses the effect. Another embodiment of the reset mechanism is to provide a means for temporarily disengaging ratchet arm 45 and housing ratchet 15 thereby permitting the sliding element 3 to be simply pushed back in a proximal direction to return it to its initial position. Another embodiment of the simulation device is constructed to permit full or partial disassembly of the simulation device in order that the elements of the simulation device can be reset to or reassembled in the initial position.

A further embodiment comprises a last-dose stop, which is not shown in the above-described simulation device. The last-dose stop is constructed to lock the button element 4 and to prevent further movement of the button element 4 in the proximal or distal direction after the dispense of the last dose has been simulated.

FIG. 5A shows a further embodiment of the simulation device made of a number of layers of cardboard in the "closed" position. The housing 1 is formed as a substantially rectangular card having guiding features which guide the travel of the sliding element 3 and the button element with respect to the housing 1. A picture of the actual device is printed on the card.

The card comprises a flap 100 suitable for covering at least a part of the card by being folded along the line 110. Opening and closing of the flap 100 can be used to simulate different states of the actual device. For example in this embodiment with the flap 100 in the "closed" position the flap 100 covers the cartridge and needle portion of the picture of the actual device. The visible outside surface of the flap 100 is printed with a picture of the cap of the actual device. Therefore in the "closed" card position the user will see a picture of the actual device in its capped state.

FIG. 5B shows the embodiment of the simulation device in an "open" position. When flap 100 is opened a portion of the picture of the actual device printed on the card is revealed. For example in this embodiment with the flap 100 in the "open" position the user will see a picture of the actual device in its uncapped state with a needle attached.

Further instructions or warning information may be printed and displayed on both the outside and inside surfaces of flap 100. For example in the embodiment of FIG. 5B the inside surface of flap 100 may carry instructions for the attachment of the needle.

In a further embodiment additional flaps, similar to flap 100, may be included. The surfaces of these flaps could be used to show additional states of the device, for example an interim uncapped state prior to needle attachment (a step to precede the illustrated embodiment of flap 100) or a subsequent needle removal stage (to follow the illustrated embodiment of flap 100). In a further embodiment these additional flaps would form a simulation device/booklet containing the full set of device user instructions. Thus the user would be able to read the instructions and simultaneously practise the use of the actual device with the simulation device.

Further information, e.g. instruction information, is also printed in a text field 501 on the card.

The button element and the sliding element 3 are also made of cardboard. The pull-push button element is positioned in the guide features of the card 1 such that the button grip 44 is visible and moveable. The button element, as shown in FIG. 5A and FIG. 5B, is in a pushed in state. The sliding element 3 is positioned in the guide features and releasably coupled to the button element such that the sliding element 3 is moved in a distal direction in response to pushing the button element distally.

The card housing 1 comprises a direction indication window 5 located at the distal end of the picture of the medication delivery device printed on the card. This direction indicating window 5 simulates a similar feature of the actual device. A status window 77 shows the position of the sliding element 3. The status window 77 is formed as cut-out in the printed cartridge holder displaying the position of the sliding element 3, the sliding element 3 simulating the travel of the bung (piston element) in the cartridge of a medication delivery device.

Further windows 8 and 9 are used to display additional information, explanation, feedback or warnings to the user during the operation of the simulation device. These further windows 8 and 9 and the information that they provide are not present in the actual medication delivery device. Any number or shape or position of these further windows may be provided in order to convey the most appropriate information regarding operation of the actual device to the user.

In the embodiment of FIG. 5A and FIG. 5B a further window 8 displays a "P" when the sliding element 3 is positioned in the starting positing. An "X" is displayed when the sliding element 3 is positioned in the final position. Information about the meaning of these symbols is printed in a text field 502. For example, the text field may contain the following text "P—Prime dose (Do not inject into body), X—Pen empty", or other information relating to indicators or symbols appearing in the window or windows.

In the embodiment of FIG. 5A and FIG. 5B a further window 9 shows a click symbol, not shown in FIG. 5, when the button grip 44 is pushed. The display of the click symbol indicates that an actual device clicks when the dose grip is pushed.

The simulation device is embodied as a disposable device with no means for resetting the simulation device to its initial position. This might be appropriate for promotional or training purposes or if every device is supplied with a simulation device serving as training aid. It is also helpful to simulate a disposable medication delivery device which is to be disposed after the last dose has been dispensed.

A further feature of the embodiment of FIG. 5A and FIG. 5B is that the simulation device becomes locked-out after the final simulated dose has been performed. This means that the button element 4 becomes locked in the pushed-in position and can no longer be pulled in order to set a further simulated dose. The same final dose lock-out is also present in the actual medication delivery device which is being simulated. Thus the simulation device and actual device will perform in a similar manner.

FIG. 6 shows an embodiment of a flat cardboard blank having solid contour lines which indicate the shape of the components 10, 3, 40 used to manufacture the simulation device as shown in FIG. 5A and FIG. 5B. The contour lines mark where to cut out the components 10, 3, 40.

The housing component 10 comprises a first part 101 forming the bottom layer of the housing, a second part 102 forming the middle layer of the housing, and a third part 103 forming the top layer of the housing. Cut-outs in the third part 103 form the windows 5, 77, 8, 9 of the housing 1.

The first and the third part 101, 103 are substantially rectangular and have the size of the card.

The second part 102 of the housing component 10 comprises a first vertical cut 21 and a second vertical cut 22. A curved third cut 23 crosses a top part of the first cut 21, forming a first and a second flap 24, 25 located on both sides of the top part of the first vertical cut 21. Parts of the card between the second cut 22 and the nearby edge are removed, forming further flaps 26, 27.

The first and second flaps 24, 25 form parts of a ratchet device. The vertical cuts 21, 22 form guiding features guiding the travel of the sliding element 3 and the button element 4 as described later.

A further part 100 of the housing component 10 located next to the second part 102 serves as flap suitable for covering at least part of the folded card. The flap 100 features an optional cut-out 78. This optional cut out permits parts of the housing component 10 which would otherwise be covered by the flap 100 to be visible to the user, more closely representing an actual injection device.

The housing component 10 comprises glue laps 29 located on one side of the third part 103 of the housing component 10. The housing 1 is manufactured by folding the housing component 10 such that the third part 103 is arranged on the second part 102 which is arranged on the first part 101. The glue laps 29 fix the folding by adhering them to the first part 101 of the housing component 100. Optionally, the third part 103 is also adhered to the second part 102 of the housing component 10.

The sliding component 3 comprises a first linear rack 301 having a set of teeth and a second linear rack 302 having a further set of teeth wherein the racks 301, 302 are arranged in parallel.

Marks 81, 82 are printed on the bottom area of the sliding component. The mark "P" will be visible in the window 8 of the housing when the sliding element 3 is positioned in the starting position. The "X" will be displayed in the window 8 of the housing when the sliding element 3 is positioned in the final position.

A button component 40 comprises a central area 400 shaped as the button element 4 including the button grip. A grip flap 401 is located next to a button grip area of the central area 400. The button component 40 comprises top and bottom flaps 402, 403 located on top and on the bottom of the button component 40, respectively. An elongated loop flap 404 having a fixing tag 405 is located on the front top of the central area 400.

A left and a right arrow mark 51, 52 are printed on the central area 400. One of the arrows 51, 52 is displayed in the direction indication window 5 of the housing 1 when the button is pulled fully out or pushed fully in, indicating whether to push or pull the button grip 44.

Figure 7A:
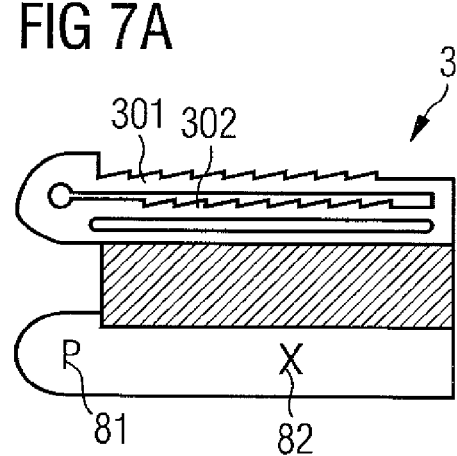
FIG. 7A shows the cut out sliding element.
Figure 7B:
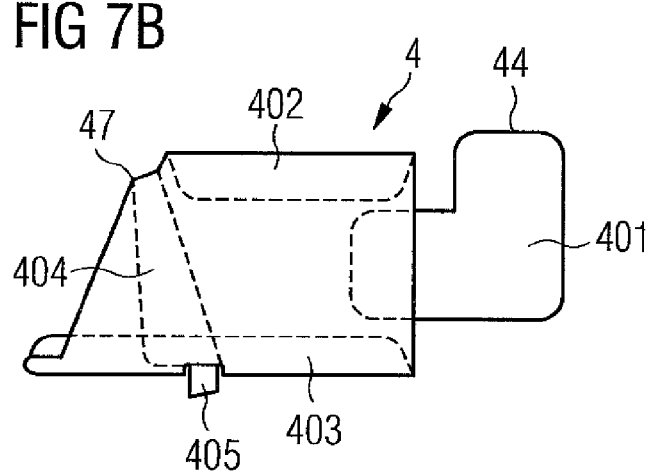
FIG. 7B shows the folded button component forming the button element.

FIG. 7A shows the cut-out sliding element 3. FIG. 7B shows the folded button component 40 forming the button element 4. The folded button element 4 is releasably coupled to the sliding element 3. For reasons of clarification the uncoupled, but folded button element 4 is shown in FIG. 7B.

The button grip 44 is formed by folding the grip flap 401 on the button grip area of the central area 400. The loop flap 404 is bent down. The fixing tag 405 is pulled through a cut-out 406 located on the bottom of the central area 400 in order to form a loop. The top and bottom flaps 402, 403 of the button component 40 are folded down. The folded loop and flaps 402, 403 form a recess guiding the travel of the sliding element 3.

Figure 8:
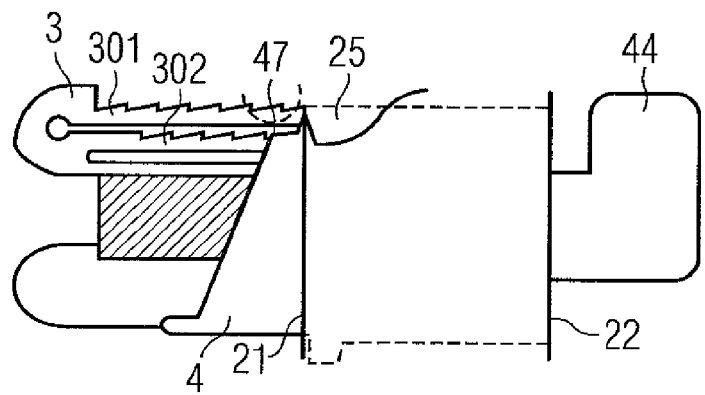
FIG. 8 shows the sliding element and the button element arranged in a guide formed in a second layer of the card housing of the simulation device shown in FIG. 5.

FIG. 8 shows the sliding element 3 and the button element 4 arranged in the guiding formed by the vertical cuts 21, 22 in the second layer 102 of the card housing 1.

The sliding element 3 is positioned in the recess formed by the bent down flaps 402, 403. Positioning is performed by pulling the loop flap 404 through the slot between the first rack 301 and the second rack 302. The loop flap 404 is bent down and fixed by pulling the fixing tab 405 through the cut-out 406. By bending down the loop flap 404 a top front corner 47 is formed slanted at an angle suitable for sliding over the teeth of the second rack 302. The corner 47 of the button element 4 and the second rack 302 form a non-return second ratchet device.

Then, the button element 4 is pulled through the first and second cuts 21, 22 such that the front and rear parts of the button element 4 are positioned in front of the middle layer 102 of the card 1 and the middle part of the button element 4 between the first and second cuts 21, 22 is located behind the middle layer 102 of the card 1.

The first flap 24 formed by the curved cut 23 is located behind the first rack 301 of the sliding element 3. The second flap 25 formed by the curved cut 23 is positioned in front of it. The second flap 25 and the first rack 301 form a non-return first ratchet device.

The sliding element 3 is prevented from travelling outwards with the button element 4 by being fixed by the non-return first ratchet device.

Simulation of the setting of a dose is performed as follows.

Before pulling the button element 4, the edge of the second flap 25 is engaged in the depression in front of a tooth of the first rack 301. The corner 47 of the button element 4 is engaged in the depression in front of a tooth of the second rack 302.

When the button element 4 is pulled, the corner 47 slides along the tooth of the second rack 302 causing the second rack 302 to bow and/or twist along its length in order to accommodate the sliding movement. Once the corner 47 has travelled beyond the tooth the second rack 302 will tend to return to its original unbowed and untwisted state whereupon the corner 47 will engage the depression in front of the next tooth. The sliding element 3 does not move in the direction of the button element 4 because the second flap 25 which is engaged in the depression in front of the tooth of the first rack 301 prevents this motion.

After pulling the button element 4 into the first position a click symbol 91, e.g. an ear symbol and the word "click", is displayed in the window 9 of the card. The click symbol 91 is located on the button element 4 such that it appears in the window 9 when the button element 4 has been pulled to the first position. Displaying the click symbol 9 simulates clicking after setting a dose.

When the button element 4 is pushed, the angle of the corner 47 causes it to bear against the tooth of the second rack 302, forcing motion of the sliding element 3 in a same direction the button element 4 is moved. When the button element 4 is pushed, the second flap 25 slides along the tooth of the first rack 301 causing the first rack 301 to bow and/or twist along its length in order to accommodate the sliding movement. Once the second flap 25 has travelled beyond the tooth the first rack 301 will tend to return to its original unbowed and untwisted state whereupon the flap 25 will engage the depression in front of the next tooth. The distal movement of the sliding element 3 is visible in the status window 77 for simulating administration of the dose.

The step-by-step travel of the sliding element 3, by pulling and pushing the button element 4, is performed until the ratchet devices have slid over the last teeth.

Once the ratchet devices have slid over the last teeth the simulation device enters a locked-out state where the button element 4 is retained in its inward position and prevented from further movement. This is achieved when the sliding element 3 has advanced to the point where loop flap 404, which is threaded between first rack 301 and second rack 302, contacts the end of the slot formed between the first rack 301 and second rack 302. At this point further movement of the button element relative to the sliding element 3 is prevented. Relative movement of the sliding element 3 to the housing 1 is prevented by the engagement of the final tooth of first rack 301 with second flap 25.

An alternative embodiment of the simulation device permits only one movement of the button element from the first to the second position. This embodiment is suitable for simulating the trigger of a single-use auto-injector.

FIGS. 9, 10, 11A and 11B show an embodiment of a simulation device which simulates attaching a needle unit, and parts of this simulation device. The simulation device comprises a slider 81 and a housing 82.

FIG. 9 shows an embodiment of the push-pull slider 81 designed to be inserted into the housing 82. One embodiment of the slider 81 is made of cardboard.

The slider 81 comprises a first information field 83 indicating a first state and a second information field 84 indicating a second state. The first information field 83 shows a hub element without a needle. The second information field 84 shows a needle unit attached to the hub element. An extending part of the slider 81 forms a handle 85. An arrow is printed on the handle 85.

FIG. 10 shows the housing 82 having a window 86. Information about the usage of the simulation device is printed in a text field 503 on the housing 82. The text field 503 may comprise the text "pull to show needle attachment".

One embodiment of the housing 82 is made of cardboard. The housing 82 comprises a top and a bottom cardboard layer. The top edges 821 and the bottom edges 822 of the layers are connected such that a guide for the slider 81 is formed. The slider 81 is located inside the housing 82 such that at least part of the handle 85 is positioned outside the housing 82.

FIG. 11A shows the slider 81 located inside the housing 82. A small part of the handle 85 and the arrowhead are visible. The first information field 83, which shows the hub element, is visible in the window 86.

The slider 81 moves into an axial direction when the handle 85 is pulled into this direction as indicated by the arrowhead so that the handle 85 is pulled out of the housing 82. Then, the second information field 84, which shows the needle unit attached, is visible in the window 86.

One embodiment of the housing 81 comprises stopping means suitable to stop further movement of the slider 81 when the second information field 84 is visible in the window 86. In one embodiment the slider is stopped by connected side edges 824 of the housing 82, the connected side edges 824 forming the stopping means.

The slider 81 moves backward when the handle 85 is pushed into the direction opposite to the pulling direction. In one embodiment the movement of the slider 81 is stopped by connected side edges 823 or side walls of the housing 82.

FIGS. 12, 13A, 13B, 13C show a simulation device comprising a rotating wheel. This simulation device is reusable and explains the steps of attaching a needle unit to a hub element when the device is prepared for injection.

FIG. 12 shows an embodiment of the wheel 91. Information fields 92, 93, 94 showing pictograms, text fields 95, 96, 97 and arrows 98 are printed on the wheel 91.

FIG. 13A shows the wheel 91 located inside a housing 82. The wheel 91 is connected with the housing 82 so that the wheel 91 is rotatable. The rotating axis of the wheel 91 is not located in the centre of the housing 82 so that a segment 91A of the wheel sticks out of the housing 82. When this segment 91A is moved in a tangential direction, the wheel 91 rotates. The arrows 98 indicate this tangential movement.

The housing 82 has a first window 86A and a second window 86B. Information for the usage of the simulation device is printed in a text field 504 on the housing 82. The text field 504 may contain the text "rotate to show needle attachment steps".

FIG. 13A shows a first state of the simulation device. The wheel 91 is positioned so that the first information field 92 is visible in the first window 86A. The corresponding first text field 95 is visible in the second window 95. The first information field 92 shows a hub element. The corresponding text field 95 explains the following step for attaching a needle. The first text field 95 may contain the text "screw needle onto device".

When the segment 91A of the wheel 91 is moved, the wheel 91 rotates. Then the second information field 93 and the corresponding second text field 96 are visible in the first and second window 86A, 86B, respectively. The arrow 98, which is visible on the segment 91A, indicates the rotation direction.

FIG. 13B shows a second state of the simulation device wherein the second information field 93 and the corresponding second text field 96 are visible. The second information field 93 shows a needle unit having a cover for protection of the needle, the needle unit being attached to the hub element. The corresponding second text field 96 explains the following step for attaching a needle. The second text field may contain the text "remove needle outer cover".

When the segment 91A of the wheel is moved, the third information field 94 and the corresponding third text field 97 are visible in the first and second window 86A, 86B, respectively.

FIG. 13C shows a third state of the simulation device, wherein the third information field 94 and the corresponding third text field 97 are visible. The third information field 94 shows an uncovered needle attached to the hub element. The corresponding third text field 96 explains the current state. The third text field may contain the text "needle ready for injection".

FIGS. 14A and 14B show a simulation device designed as a pop-up card. FIG. 14A shows the folded pop-up card. FIG. 14B shows the open pop-up card.

Pop-up cards can be made of cardboard. The pop-up card comprises plane elements connected such that the folded card is flat and the open pop-up card turns into a three dimensional arrangement.

The card comprises a card top 201 and a card bottom 202 connected via a fold forming a first hinge 205. When the card is opened the card top 201 rotates relative to the card bottom 202 around the first hinge 205.

The card comprises a pop-up element having a top element 211 and a bottom element 212 connected via a fold forming a second hinge 215. The top element 211 is connected with the card top 201 via a third hinge 216. The bottom element 212 is connected with the card bottom 202 via a fourth hinge 217. In one embodiment the top and bottom elements 211, 212 comprise laps located on the edge opposite the second hinge 215, the laps being folded. By gluing the laps to the card top and bottom 201, 202, the third and forth hinge 216, 217 are formed.

If the card is folded the top element 211 of the pop-up element is folded on the bottom element 212. These elements 211, 212 are sandwiched between the card top 201 and the card bottom 202. The third and fourth hinge 216, 21 are located between the first and the second hinge 205, 215.

When the pop-up card is opened, the card top 201 rotates into a first direction relative to the card bottom 202 around the first hinge 205. The top element 211 of the pop-up element rotates into a second direction relative to the bottom element 212, the second direction being opposite to the first direction.

When the card top 201 has rotated through 90 degrees, the top element 211 of the pop-up element is positioned parallel or nearly parallel to the card bottom 202 and the bottom element 212 of the pop-up element is positioned parallel or nearly parallel to the card top 201. Opening the pop-up card transforms the flat folded card into a three dimensional arrangement, wherein the pop-up element is formed similar to an actual device, e.g. a delivery pen. In one embodiment the pop-up element is printed in order to resemble the actual device.

FIGS. 15A and 15B show an embodiment having a hinged section 233. This embodiment comprises a plane unit 231 and a lever 232. The plane unit 231 and the lever 232 are connected via the hinged section 233. The hinged section 233 is connected to the plane unit 231 via a first hinge 234 and to the lever 232 via a second hinge 235. The first hinge 234 and the second hinge 235 are arranged parallel.

If the arrangement is folded, the hinged section 233 is sandwiched between the plane unit 231 and the lever 232. When the lever 231 is pulled into an axial direction which is the direction from the second hinge 235 to the first hinge 234 the hinged section 233 rotates relative to the plane unit 231 into a first direction (e.g. clockwise) and the lever 232 rotates relative to the hinged section 233 into a second direction (e.g. counter clockwise) opposite to the first direction. Due to the rotation the hinged section 233 rotates and the lever 232 is lifted away from the plane unit 231.

When the lever 232 is moved backwards into the direction opposite to the pulling direction, the hinged section 233 rotates relative to the plane unit 231 into the second direction and the lever 232 rotates relative to the hinged section 233 into the first direction. The arrangement is folded so that the hinged section 233 is sandwiched between the back unit 231 and the lever 232.

The above describe arrangement is suitable for simulating moveable parts of a device.

FIGS. 16A and 16B show an arrangement with angled folds. The arrangement comprises a plane unit 231 and a lever 232. A hinged section comprises a first, a second and a third triangular section 241, 242, 243, each formed as an isosceles right triangle. One side of the first triangular section 241 is connected to the plane unit 231 via a first hinge 251. The hypotenuse of the second triangular section 242 is connected to the hypotenuse of the first triangular section 241 via a second hinge 252. A side of the third triangular section 243 is connected to a side of the second triangular section 242 via a third hinge 253. The hypotenuse of the third triangular section 243 is connected with the lever 232 via a fourth hinge 254.

FIG. 16A shows the folded arrangement. FIG. 16B shows the open arrangement after pulling the lever 232 into an axial direction. FIG. 16B shows that the first and third hinge 251, 253 are arranged orthogonal to the pulling direction. The second and forth hinge 252, 254 are arranged angled.

The lever 232 and the hinged sections 241, 242, 243 are made of a folded stripe having three folds forming the second, third and fourth hinge 252, 253, 254. Dashed lines indicate to fold in one direction and the dotted line indicates to fold into the opposite direction to form the folds.

When the lever 232 is pulled the triangular sections 241, 242, 243 rotate around the hinges 251, 252, 253, 254 so that the lever 232 and the triangular sections 241, 242, 243 are located adjacent to each other in a same plane or almost a same plane.

After the lever 232 has been pulled, the second and third triangular section 242, 243 have been rotated through 90 degrees, but in opposite directions.

FIG. 17 shows a further embodiment of an arrangement with angled folds. The arrangement differs from the arrangement shown in FIGS. 16A and 16B by a stripe 244 arranged on the second triangular section 242. When the arrangement is folded the stripe 244 extends in a direction orthogonal to the pulling direction.

When the lever 232 is pulled, the stripe 244 rotates in the same direction as the second triangular section 242 rotates. When the lever 232 is moved backwards, the stripe 244 moves back into its initial position.

The above-mentioned simulation device is used to simulate rotating parts of a device.

One embodiment of a simulation card as shown in FIGS. 5A and 5B further comprises pop-up elements and/or folded elements as shown in FIGS. 14A, 14B, 15A, 15B, 16A, 16B and 17.

A further embodiment of a simulation device comprises a flap which suddenly flips over when a user pulls a lever coupled with the flap.

Embodiments of pop-up arrangements and folded arrangements contain electronic sound effects. Electronic devices comprising a chip, a speaker and a battery are suitable to generate the sound effects, which may be similar to sound effects used in greeting cards.

In one embodiment the sound effects are triggered at significant stages of simulated use. In one embodiment the sound effect, e.g. a click, is produced as audible feedback. In one embodiment the sound effects are verbal instructions, feedbacks or warnings.

FIG. 18A, 18B, 18C and 18D show an embodiment of a simulation device which simulates a dry powder disk inhaler. This simulation device is suitable to train inhalers.

The simulation device is configured to simulate opening and closing of an outer cover, movement of an actuation lever and countdown of a dose counter.

The simulation device comprises a housing 600 with a grip section 620 and an outer cover 610. The housing 600 comprises a window 630 for indicating dose information. In this case the initial dose information "60", which means 60 doses are available, is indicated. A rotatable dose counter wheel 635 is located inside the housing 600. Numbers for indicating the dose information are provided on the dose counter wheel 635. The dose information shown in the window 630 depends on the position of the dose counter wheel 635 relative to the window 630.

One embodiment of the simulation device has the same size and the same two dimensional shape as an actual device. An alternative embodiment is designed as an instruction card which is larger than the actual device. Such an instruction card comprises multiple card layers having a central rivet or stud acting as pivot for rotating layers. One embodiment of the simulation device comprises a ratchet that may be embodied as non-return ratchet.

The rotatable outer cover 610 comprises a message window 640 which is not provided in an actual device.

Figure 18A:
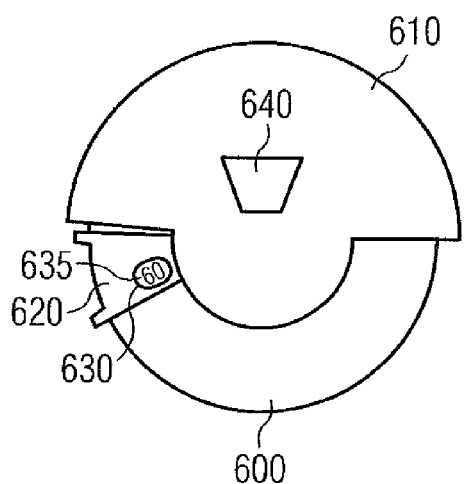

FIG. 18A shows the outer cover 610 in a closed position. A text field providing user information is visible in the message window 640. The text field may contain the text "remove cover to open".

A movable actuation lever 650 and a mouthpiece 670 (not shown in FIG. 18A, but in FIG. 18B) are located beneath the closed outer cover 610.

The outer cover 610 is coupled with the actuation lever 650 which is located beneath the actuation cover 610. In one embodiment the actuation lever 650 is engaged in a fold or latch in the outer cover 610.

When the outer cover 610 is opened, the outer cover 610 pulls the actuation lever 650 into a first position (unset position). This relative movement of the actuation lever 650 cannot be seen by the user as it is concealed behind outer cover 610. Once the actuation lever reaches the first position, the outer cover 610 bumps out of contact with the actuation lever 650 and is free to continue rotating.

Figure 18C:
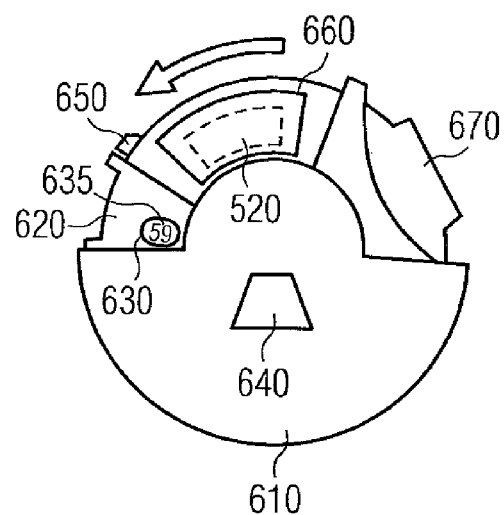
Figure 18B:
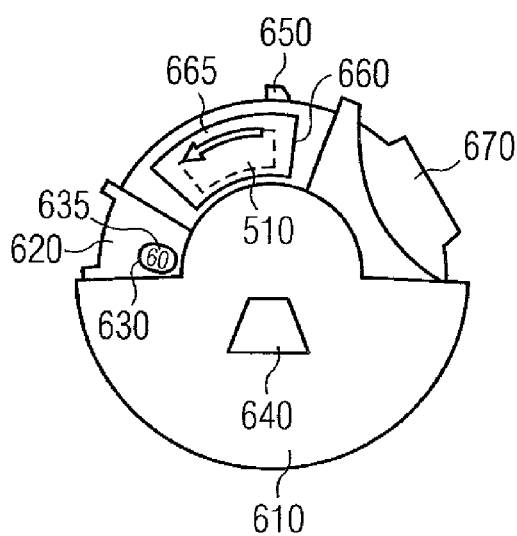

FIG. 18B shows the simulation device after opening the outer cover 610.

The outer cover 610 has rotated into an open position. Due to the rotation another text field is visible in the message window 640. The text field may contain the text "rotate cover to close".

A second message window 660 located near the actuation lever 650 provides user information. First information is shown if the actuation lever 650 is located in the first position as shown in FIG. 18B. Second information is shown when the actuation lever 650 is located in a second position. In one embodiment the actuation lever 650 is coupled to a rotatable wheel 665 containing the first information and the second information, the wheel 665 being located inside the housing 600. The first and second information is printed on the wheel 665 as text and/or pictograms.

In one embodiment the message window 660 shows a first text field 510 containing "pull lever to set dose" and an arrow indicating the direction in which the actuation lever 650 is moved into the second position.

For simulating setting a dose the actuation lever 650 is moved into the second position. The actuation lever 650 is rotated through an angle, e.g. 30 degrees.

FIG. 18C shows the simulation device after moving the actuation lever 650 into the second position (set position).

When the actuation lever 650 moves to the second position another text field 520 is shown in the second message window 660. The text field 520 may contain the text "ready to inhale".

The actuation lever 650 and/or the wheel 665 are connected to the dose counter wheel 635 via a lost motion component. A lost motion component is configured to transform an input movement into a smaller output movement. In one embodiment the dose counter wheel 635 rotates through a smaller angle than the angle through which the actuation lever 650 rotates, e.g. when the actuation lever 650 rotates through 30 degrees the dose counter wheel 635 merely rotates through six degrees. Due to the rotation of the dose counter wheel 635 the dose information shown in the window 630 changes.

Figure 18D:
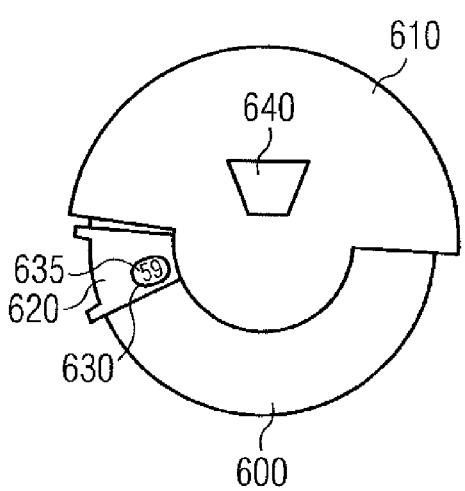

FIG. 18D shows the simulation device after closing of the outer cover 610. Unseen by the user, the actuation lever 650 remains in the second position. (This is unlike the actual device where the mechanism resets the lever at this point). The outer cover 610 bumps over the actuation lever 650. Thus, the outer cover 610 is in contact with the actuation lever and ready to move the actuation lever 650 the next time the outer cover 610 is opened.

The user can repeat the above described simulation until the dose counter has reached 0. Then, the counter wheel disengages and remains at 0.

Other implementations are within the scope of the claims. Elements of different embodiments may be combined to form implementations not specifically described herein.

REFERENCE NUMERALS 1 housing
2 slot
13 housing cover
3 sliding element
4 button element
44 button grip
5 direction indication window
6 hub element
7 display element
8, 9 window
10 housing component
11 bottom part of the housing
12 housing wall section
13, 14 housing cover
15 housing arm
31, 32, 33, 39 ratchet teeth
21, 22, 23 cut
24, 25, 26, 27 flap
29 glue lap
40 button component
61 bottom part of the hub element
62 top part of the hub element
41 part of the button element
42 middle part of the button section
43 locking element
45 extended ratchet arm
47 corner
51, 52, 81, 82, 91 marks
71 dose scale
77 status window
78 window in the flap
81 slider
82 housing
83 first information field
84 second information field
85 handle
86, 86A, 86B window
91 rotating wheel
91A segment of the wheel
92, 93, 94 information field
95, 96, 97 text field
98 arrow
100 flap
101, 102, 103 layer of the housing
110 folding line
122 inside wall
123 stopping corner
201, 202 card top, bottom card
211, 212 top, bottom element
205, 215, 216, 217 hinge
231 plane unit
232 lever
233 hinged section
234, 235 hinge
241, 242, 243 triangular section
244 stripe
251, 252, 253, 254 hinge
301, 302 rack with teeth
400 central area
401, 402, 403 flap
404 loop flap
405 fixing tag
406 cut out
441 bottom part of the button grip
442 middle part of the button grip
443 top part of the button grip
501, 502, 503, 504, 510, 520 text field
600 housing
610 outer cover 630 window
635 dose counter wheel
640, 660 message window
650 actuation lever
665 wheel
670 mouthpiece
821 top edges
822 bottom edges
823, 824 side edges

The invention claimed is:

1. Simulation device for simulating the operation of a medication delivery device comprising
a housing, wherein the housing is formed as a card having at least two layers, and
a moveable element partly disposed in the housing, the moveable element being moveable from a first position to a second position,
a sliding element at least partly disposed in the housing having a distal end and a proximal end, and
a display element configured to display status information and/or instruction information which changes when the sliding element and/or a wheel and/or the moveable element move, wherein the status information and/or instruction information comprises a number of simulated doses remaining or an amount of simulated medicament remaining in the simulation device, and
wherein the moveable element is coupled to the sliding element such that the sliding element is moved in a direction to the distal end in response to moving the moveable element from the first position to the second position.

2. Simulation device according to claim 1, wherein the moveable element simulates a needle unit, a cap, a trigger, a slider, a medication cartridge or cartridge holding component, a device cover or a button.

3. Simulation device according to claim 1, wherein a sliding element is constructed to move from a starting position to a final position.

4. Simulation device according to claim 3, wherein the sliding element is resettable to the starting position.

5. Simulation device according to claim 3, wherein the sliding element is not resettable to the starting position.

6. Simulation device according to claim 3, wherein
the movement of the moveable element is blocked when the sliding element reaches the final position.

7. Simulation device according to claim 1 comprising a ratchet device releasably engaging the sliding element.

8. Simulation device according to claim 7, wherein
the ratchet device is constructed such that the sliding element does not move into a proximal direction in response to moving a button element proximally from the second position to the first position.

9. Simulation device according to claim 1, comprising
a spring element coupled to a button element and/or to a sliding element.

10. Simulation device according to claim 1, wherein
the display element is suitable for displaying the position of the sliding element.

11. Simulation device according to claim 1, comprising
at least one second display element constructed to display status information which corresponds to the position of the sliding element.

12. Simulation device according to claim 11, wherein
a starting status mark is displayed when the sliding element is positioned in the starting position and/or
a final status mark is displayed when the sliding element is positioned in the final position.

13. Simulation device according to claim 11, comprising
at least one third display element constructed to display status information which corresponds to the position of the moveable element.

14. Simulation device according to claim 13, wherein
a first direction mark is displayed when the moveable element is positioned in the first position and/or
a second direction mark is displayed when the moveable element is positioned in the second position.

15. Simulation device according to claim 1, further comprising at least one display element comprising a window.

16. Simulation device according to claim 15, wherein
the window is covered with a transparent material comprising a scale.

17. Simulation device according to claim 1, comprising
a hub element suitable for simulating the releasable attachment of a needle unit.

18. Simulation device according to claim 1, comprising means for generating sound effects.

19. Simulation device according to claim 1, wherein
at least one component of the simulation device is made of plastic, a laminated composite foam-board, paper or cardboard.

20. Simulation device according to claim 19, wherein at least one of the components is folded.

21. Simulation device according to claim 20, wherein
the folded component comprises rotatable parts.

22. Simulation device according to claim 1, comprising
a hinged element connected to the simulation device via a hinge and to a lever such that the hinged element rotates when the lever is moved.

23. Simulation device according to claim 1 comprising
at least one hinged flap suitable for covering at least part of the housing.

24. Simulation device according to claim 1, further comprising
pop-up elements.

25. Simulation device according to claim 1, suitable for simulating multiple devices within one housing.

* * * * *